(12) United States Patent
Kanazawa et al.

(10) Patent No.: US 10,707,398 B2
(45) Date of Patent: Jul. 7, 2020

(54) N-TYPE THERMOELECTRIC CONVERSION LAYER, THERMOELECTRIC CONVERSION ELEMENT, AND COMPOSITION FOR FORMING N-TYPE THERMOELECTRIC CONVERSION LAYER

(71) Applicant: FUJIFILM Corporation, Tokyo (JP)

(72) Inventors: Yoshinori Kanazawa, Ashigara-kami-gun (JP); Yuzo Nagata, Ashigara-kami-gun (JP); Hiroki Sugiura, Ashigara-kami-gun (JP); Naoyuki Hayashi, Ashigara-kami-gun (JP); Kimiatsu Nomura, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 76 days.

(21) Appl. No.: 16/009,509

(22) Filed: Jun. 15, 2018

(65) Prior Publication Data
US 2018/0294396 A1 Oct. 11, 2018

Related U.S. Application Data

(63) Continuation of application No. PCT/JP2016/086840, filed on Dec. 12, 2016.

(30) Foreign Application Priority Data

Dec. 18, 2015 (JP) .................................. 2015-247599
Jan. 18, 2016 (JP) .................................. 2016-006990

(51) Int. Cl.
*H01L 35/12* (2006.01)
*H01L 35/24* (2006.01)
(Continued)

(52) U.S. Cl.
CPC ............ *H01L 35/24* (2013.01); *C07C 211/07* (2013.01); *C07C 211/08* (2013.01);
(Continued)

(58) Field of Classification Search
CPC ...................................................... H01L 35/24
See application file for complete search history.

(56) References Cited

U.S. PATENT DOCUMENTS

| | | |
|---|---|---|
| 2008/0191606 A1 | 8/2008 | Geohegan et al. |
| 2009/0044848 A1 | 2/2009 | Lashmore et al. |

(Continued)

FOREIGN PATENT DOCUMENTS

| | | | |
|---|---|---|---|
| JP | 2010-515227 A | 5/2010 | |
| JP | 2010-537410 A | 12/2010 | |

(Continued)

OTHER PUBLICATIONS

Pandurangappa (the chapter "Chemically Modified Carbon Nanotubes: Derivatization and their Applications" in the book "Carbon Nanotubes Applications on Electron Devices"). (Year: 2011).*

(Continued)

*Primary Examiner* — Angelo Trivisonno
(74) *Attorney, Agent, or Firm* — Sughrue Mion, PLLC

(57) ABSTRACT

An object of the present invention is to provide an n-type thermoelectric conversion layer, which has a high power factor and exhibits excellent performance stability, a thermoelectric conversion element including the n-type thermoelectric conversion layer, and a composition for forming an n-type thermoelectric conversion layer used in the n-type thermoelectric conversion layer. The n-type thermoelectric conversion layer of the present invention contains carbon nanotubes and an amine compound which is represented by General Formula (1) or (2) and has a C log P value of 2.0 to 8.2.

(Continued)

$$X_m\text{—}N\text{—}R_n \quad (1)$$

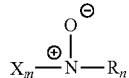

(2)

10 Claims, 3 Drawing Sheets

(51) Int. Cl.
  *H01L 35/32* (2006.01)
  *H01L 35/34* (2006.01)
  *C07C 291/04* (2006.01)
  *H01L 35/22* (2006.01)
  *C07C 215/08* (2006.01)
  *C07C 211/07* (2006.01)
  *C07C 211/08* (2006.01)
  *C07C 215/12* (2006.01)
  *B82Y 30/00* (2011.01)

(52) U.S. Cl.
  CPC .......... *C07C 215/08* (2013.01); *C07C 215/12* (2013.01); *C07C 291/04* (2013.01); *H01L 35/22* (2013.01); *H01L 35/32* (2013.01); *H01L 35/34* (2013.01); *B82Y 30/00* (2013.01); *Y10S 977/742* (2013.01); *Y10S 977/948* (2013.01)

(56) References Cited

U.S. PATENT DOCUMENTS

2013/0081678 A1  4/2013  Naito et al.
2016/0013392 A1  1/2016  Takahashi et al.

FOREIGN PATENT DOCUMENTS

JP   2011-527809 A   11/2011
JP   2013-80565 A    5/2013
JP   2014-209573 A   11/2014

OTHER PUBLICATIONS

International Search Report dated Mar. 7, 2017 issued by the International Searching Authority in No. PCT/JP2016/086840.
International Preliminary Report on Patentability with the translation of Written Opinion dated Jun. 19, 2018 issued by the International Bureau in No. PCT/JP2016/086840.
Communication dated Jul. 23, 2019, from the Japanese Patent Office in counterpart application No. 2017-556035.
Office Action dated Feb. 18, 2020, from the Japanese Patent Office in Japanese Application No. 2017-556035.

\* cited by examiner

N-TYPE THERMOELECTRIC CONVERSION LAYER, THERMOELECTRIC CONVERSION ELEMENT, AND COMPOSITION FOR FORMING N-TYPE THERMOELECTRIC CONVERSION LAYER

CROSS-REFERENCE TO RELATED APPLICATIONS

This application is a Continuation of PCT International Application No. PCT/JP2016/086840 filed on Dec. 12, 2016, which claims priority under 35 U.S.C. § 119(a) to Japanese Patent Application No. 2015-247599 filed on Dec. 18, 2015 and Japanese Patent Application No. 2016-006990 filed on Jan. 18, 2016. Each of the above applications is hereby expressly incorporated by reference, in its entirety, into the present application.

BACKGROUND OF THE INVENTION

1. Field of the Invention

The present invention relates to an n-type thermoelectric conversion layer, a thermoelectric conversion element, and a composition for forming an n-type thermoelectric conversion layer.

2. Description of the Related Art

Thermoelectric conversion materials that enable the interconversion of thermal energy and electric energy are used in power generating elements generating electric power from heat or thermoelectric conversion elements such as a Peltier element. Thermoelectric conversion elements can convert thermal energy directly into electric power, do not require a moving portion, and are used in, for example, wrist watches operating by body temperature, power supplies for backwoods, and aerospace power supplies.

The thermoelectric conversion materials are roughly classified into two types including a p-type thermoelectric conversion material and an n-type thermoelectric conversion material. Generally, as the n-type thermoelectric conversion material, an inorganic material such as nickel is known. Unfortunately, the inorganic material is expensive, contains toxic substances, and needs to undergo a complicated process for being made into a thermoelectric conversion element.

Therefore, in recent years, techniques using carbon materials represented by carbon nanotubes (hereinafter, referred to as "CNT" as well) have been suggested. For example, JP2014-209573A discloses an aspect in which an n-type thermoelectric conversion material is provided by adding a dopant such as an amine compound as an n-type dopant to carbon nanotubes (claims, paragraphs "0181" and "0225", and the like).

SUMMARY OF THE INVENTION

Meanwhile, in recent years, in order to improve the performance of instruments using thermoelectric conversion elements, further improvement of the thermoelectric conversion performance of the thermoelectric conversion elements has been required. Furthermore, the thermoelectric conversion elements have been required not to easily show the change of the thermoelectric conversion performance even in a case where they are exposed to a high-temperature and high-humidity environment (moisture-heat environment), such that the thermoelectric conversion elements can be used in various environments.

In line with this trend, based on JP2014-209573A, the inventors of the present invention doped carbon nanotubes by using an amine compound and prepared an n-type thermoelectric conversion layer by using the obtained composition as a thermoelectric conversion material. As a result, it was revealed that the n-type thermoelectric conversion layer does not always satisfy the thermoelectric conversion performance (particularly, a power factor (hereinafter, referred to as "PF" as well)) that is currently required. Furthermore, it was revealed that, in a case where the n-type thermoelectric conversion layer is exposed to a moisture-heat environment, sometimes the thermoelectric conversion performance such as a Seebeck coefficient deteriorates, and the performance stability becomes insufficient.

The present invention has been made in consideration of the circumstances described above, and an object of the present invention is to provide an n-type thermoelectric conversion layer which has a high power factor and excellent performance stability, a thermoelectric conversion element including the n-type thermoelectric conversion layer, and a composition for forming an n-type thermoelectric conversion layer used in the n-type thermoelectric conversion layer.

In order to achieve the aforementioned object, the inventors of the present invention conducted an intensive examination. As a result, the inventors have found that in a case where an amine compound, which is represented by a specific general formula and has a partition coefficient within a specific range, is used as an n-type dopant, the aforementioned object can be achieved.

That is, the inventors of the present invention have found that the aforementioned object can be achieved by the following constitutions.

(1) An n-type thermoelectric conversion layer comprising carbon nanotubes and an amine compound which is represented by General Formula (1) or (2) which will be described later and has a C log P value of 2.0 to 8.2.

(2) The n-type thermoelectric conversion layer described in (1), in which the amine compound is represented by General Formula (1), and m in General Formula (1) is 1.

(3) The n-type thermoelectric conversion layer described in (1) or (2), in which a boiling point of the amine compound is equal to or higher than 200° C.

(4) A thermoelectric conversion element comprising the n-type thermoelectric conversion layer described in any one of (1) to (3).

(5) The thermoelectric conversion element described in (4), further comprising a p-type thermoelectric conversion layer electrically connected to the n-type thermoelectric conversion layer, in which the p-type thermoelectric conversion layer contains carbon nanotubes.

(6) A composition for forming an n-type thermoelectric conversion layer comprising carbon nanotubes and an amine compound which has a C log P value of 2.0 to 8.2 and is represented by General Formula (1) or (2) which will be described later.

As will be described below, according to the present invention, it is possible to provide an n-type thermoelectric conversion layer which has a high power factor and exhibits excellent performance stability, a thermoelectric conversion element including the n-type thermoelectric conversion layer, and a composition for forming an n-type thermoelectric conversion layer used in the n-type thermoelectric conversion layer.

DESCRIPTION OF THE PREFERRED EMBODIMENTS

Figure 1:
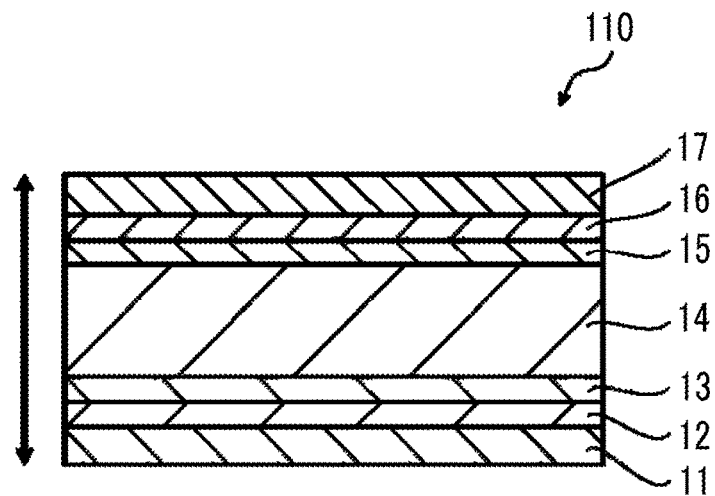
FIG. 1 is a cross-sectional view of a first embodiment of a thermoelectric conversion element of the present invention.

Hereinafter, the n-type thermoelectric conversion layer, the thermoelectric conversion element, and the composition for forming an n-type thermoelectric conversion layer of the present invention will be described.

In the present specification, "(meth)acrylate" represents either or both of acrylate and methacrylate, and includes a mixture of these.

In the present specification, a range of numerical values described using "to" means a range that includes numerical values listed before and after "to" as a lower limit and an upper limit.

First, the characteristics of the n-type thermoelectric conversion layer of the present invention will be described.

One of the characteristics of the n-type thermoelectric conversion layer of the present invention is that the n-type thermoelectric conversion layer contains carbon nanotubes and an amine compound (hereinafter, referred to as "specific amine compound" as well) which is represented by a specific general formula and has a partition coefficient within a specific range.

Presumably, in the n-type thermoelectric conversion layer of the present invention, the aforementioned specific amine compound may interact with the carbon nanotubes and change the carbon nanotubes into an n-type by doping them. As is evident from General Formula (1) or (2) which will be described later, the specific amine compound has a linear or branched unsubstituted alkyl group. Furthermore, as will be described later, the amine compound has a partition coefficient which is equal to or greater than a specific value and has high hydrophobicity. Presumably, for this reason, the aforementioned alkyl group may have strong interaction (for example, hydrophobic interaction) with the carbon nanotubes and make the aforementioned doping reliable. That is, the alkyl group is considered to function as a group adsorbed onto the carbon nanotubes.

It is considered that, as a result, the n-type thermoelectric conversion layer of the present invention may exhibit a high power factor. As will be shown in comparative examples which will be described later, in a case where an amine compound is used which does not have a linear or branched unsubstituted alkyl group (Comparative Examples 3 and 4) or in a case where an amine compound is used which has a linear or branched unsubstituted alkyl group and a partition coefficient smaller than a predetermined value (Comparative Example 2), a power factor becomes insufficient. From this result, it is possible to infer that the n-type thermoelectric conversion layer of the present invention exhibits a high power factor.

Meanwhile, from the examination performed by the inventors of the present invention, the inventors obtained knowledge that in a case where an extremely hydrophobic compound is used as an amine compound, when the n-type thermoelectric conversion layer is exposed to a moisture-heat environment for a long period of time, the amine compound slowly oozes out the layer (bleed out), and hence the thermoelectric conversion performance such as a Seebeck coefficient changes. Specifically, it was clearly revealed that in a case where an amine compound, such as octadecylamine used in Comparative Example 1 which will be described later, having an extremely high partition coefficient is used, the aforementioned problem occurs, and the performance stability becomes insufficient. In the present invention, considering the above knowledge, a compound having a partition coefficient equal to or smaller than a specific value is used as an amine compound.

It is considered that because an amine compound (specific amine compound), which is represented by a specific general formula and has a partition coefficient within a specific range, is used in the present invention as described above, a high power factor and excellent performance stability may be obtained.

n-Type Thermoelectric Conversion Layer

The n-type thermoelectric conversion layer of the present invention contains carbon nanotubes and an amine compound which is represented by General Formula (1) or (2) which will be described later and has a C log P value of 2.0 to 8.2.

First, each of the components contained in the n-type thermoelectric conversion layer of the present invention will be described, and then a method for manufacturing the n-type thermoelectric conversion layer of the present invention will be described.

Carbon Nanotubes

Carbon nanotubes (CNT) contained in the n-type thermoelectric conversion layer of the present invention include single-layer CNT formed of one sheet of carbon film (graphene sheet) wound in the form of a cylinder, double-layered CNT formed of two graphene sheets wound in the form of concentric circles, and multilayered CNT formed of a plurality of graphene sheets wound in the form of concentric circles. In the present invention, the n-type thermoelectric conversion layer may contain one kind of each of the single-layer CNT, the double-layered CNT, and the multilayered CNT singly, or two or more kinds thereof in combination. Particularly, the n-type thermoelectric conversion layer preferably contains the single-layer CNT having excellent properties in terms of electric conductivity and semiconductor characteristics or the double-layered CNT, and more preferably contains the single-layer CNT.

The n-type thermoelectric conversion layer may contain semiconductive single-layer CNT or metallic single-layer CNT, or contain both of them in combination. Furthermore, CNT may contain a metal or the like, and the n-type thermoelectric conversion layer may contain CNT containing a fullerene molecule and the like (particularly, CNT containing fullerene is called a pivot) may be used.

CNT can be manufactured by an arc discharge method, a chemical vapor deposition method (hereinafter, referred to as a CVD method), a laser-ablation method, and the like. CNT used in the n-type thermoelectric conversion layer of the present invention may be obtained by any method, but it is preferable to use CNT obtained by the arc discharge method and the CVD method.

At the time of manufacturing CNT, fullerene or graphite and amorphous carbon are also generated as by-products in some cases. In order to remove these by-products, CNT may be purified. The CNT purification method is not particularly limited, and examples thereof include methods such as washing, centrifugation, filtration, oxidation, and chromatography. In addition, an acid treatment using nitric acid, sulfuric acid, and the like and an ultrasonic treatment are also effective for removing impurities. Furthermore, from the viewpoint of improving purity, it is more preferable to separate and remove impurities by using a filter.

In a case where CNT is manufactured and used for manufacturing the n-type thermoelectric conversion layer of the present invention, CNT obtained after purification may be used as it is. Furthermore, because CNT is generally generated in the form of strings, CNT may be used after being cut in the desired length according to the purpose. By an acid treatment using nitric acid, sulfuric acid, or the like, an ultrasonic treatment, a freezing and pulverizing method, and the like, CNT can be cut in the form of short fiber. From the viewpoint of improving purity, it is also preferable to collectively separate CNT by using a filter.

In a case where CNT is used for manufacturing the n-type thermoelectric conversion layer of the present invention, not only cut CNT but also CNT prepared in the form of short fiber can also be used.

The average length of CNT is not particularly limited. However, from the viewpoint of ease of manufacturing, film formability, electric conductivity, and the like, the average length is preferably 0.01 to 1,000 μm, and more preferably 0.1 to 100 μm.

The diameter of the single-layer CNT used in the present invention is not particularly limited. From the viewpoint of durability, film formability, electric conductivity, thermoelectric performance, and the like, the diameter of the single-layer CNT is preferably equal to or greater than 0.5 nm and equal to or smaller than 4.0 nm, more preferably equal to or greater than 0.6 nm and equal to or smaller than 3.0 nm, and even more preferably equal to or greater than 0.7 nm and equal to or smaller than 2.0 nm. The diameter distribution of 70% or more of CNT (hereinafter, "diameter distribution of 70% or more" will be simply described as "diameter distribution" as well) is preferably within 3.0 nm, more preferably within 2.0 nm, even more preferably within 1.0 nm, and particularly preferably within 0.7 nm. The diameter and the diameter distribution can be measured by the method which will be described later.

Sometimes CNT used in the present invention includes defective CNT. The defect of CNT results in the deterioration of the electric conductivity of a dispersion for a thermoelectric conversion layer and the like. Therefore, it is preferable to reduce the defect. The amount of the defect of CNT can be estimated by an intensity ratio G/D (hereinafter, referred to as a G/D ratio) between a G-band and a D-band in a Raman spectrum. In a case where a CNT material has a high G/D ratio, the material can be estimated as having a small amount of defects. Particularly, in a case where single-layer CNT is used, the G/D ratio is preferably equal to or higher than 10 and more preferably equal to or higher than 30.

Calculation of Diameter and Diameter Distribution of Single-Layer Carbon Nanotubes In the present specification, the diameter of single-layer carbon nanotubes is evaluated as below. That is, a Raman spectrum of the single-layer carbon nanotubes is measured using excitation light of 532 nm (excitation wavelength: 532 nm), and by a shift ω (RBM) (cm$^{-1}$) of a radial breathing mode (RBM), the diameter of the single-layer CNT is calculated using the following calculation formula. The value calculated from a maximum peak was taken as the diameter of CNT. The diameter distribution was obtained from the distribution of each peak top.

Calculation formula: Diameter (nm)=248/ω(RBM)

In the n-type thermoelectric conversion layer of the present invention, the content of the carbon nanotubes is not particularly limited. However, in the n-type thermoelectric conversion layer, the content of the carbon nanotubes is preferably 5% to 95% by mass, more preferably 30% to 90% by mass, and even more preferably 40% to 80% by mass.

One kind of CNT may be used singly, or two or more kinds of CNT may be used in combination.

Specific Amine Compound

The amine compound contained in the n-type thermoelectric conversion layer of the present invention is an amine compound (specific amine compound) which is represented by General Formula (1) or (2) shown below and has a C log P value of 2.0 to 8.2. The n-type thermoelectric conversion layer may contain one kind of specific amine compound singly, or two or more kinds of specific amine compounds in combination.

First, the general formula will be described, and then the C log P value will be described.

General Formula

In General Formulae (1) and (2), X represents a linear or branched unsubstituted alkyl group.

R represents a hydrogen atom or an alkyl group which may have a substituent.

m represents an integer of 1 to 3. In a case where m is an integer equal to or greater than 2, a plurality of X's may be the same as or different from each other. n represents an integer of 0 to 2. In a case where n is an integer equal to or greater than 2, a plurality of R's may be the same as or different from each other and may form a ring by being bonded to each other. m and n satisfy a relation equation of m+n=3.

As described above, in General Formulae (1) and (2), X represents a linear or branched unsubstituted alkyl group. The number of carbon atoms in the alkyl group is not particularly limited, but is preferably 1 to 30, more preferably 3 to 20, even more preferably 6 to 18, and particularly preferably 10 to 16.

Specific examples of the linear or branched unsubstituted alkyl group include a methyl group, an ethyl group, a propyl group, a butyl group, a pentyl group, a hexyl group, a heptyl group, an octyl group, a nonyl group, a decyl group, an undecyl group, a dodecyl group, a hexadecyl group, an octadecyl group, and the like.

As described above, in General Formulae (1) and (2), R represents a hydrogen atom or an alkyl group which may have a substituent.

The number of carbon atoms in "alkyl group which may have a substituent" represented by R is not particularly limited, but is preferably 1 to 10, more preferably 1 to 5, and even more preferably 1 or 2. The alkyl group may be linear, branched, or cyclic.

The substituent of "alkyl group which may have a substituent" represented by R is not particularly limited. Specific examples of the substituent include a substituent W which will be described later.

The substituent is preferably a hydrophilic group. Examples of the hydrophilic group include a hydroxy group, a cyano group, a carboxy group, an amino group, an amide group, and the like. Among these, a hydroxy group is preferable.

"Alkyl group which may have a substituent" represented by R is preferably a group other than "linear or branched unsubstituted alkyl group".

As described above, in General Formulae (1) and (2), m represents an integer of 1 to 3. m represents the number of X's substituting the nitrogen atom in General Formulae (1) and (2). m is preferably an integer of 1 or 2, and more preferably 1.

In a case where m is an integer equal to or greater than 2, a plurality of X's may be the same as or different from each other.

As described above, in General Formulae (1) and (2), n represents an integer of 0 to 2. n represents the number of R's substituting the nitrogen atom in General Formulae (1) and (2).

In a case where n is an integer equal to or greater than 2, a plurality of R's may be the same as or different from each other and may form a ring by being bonded to each other.

For example, the amine compound used in Example 17, which will be described later, is represented by General Formula (1) in which n is 2 and two R's form a ring by being bonded to each other.

As described above, m and n in General Formulae (1) and (2) satisfy a relation equation of m+n=3.

C log P Value

The specific amine compound has a C log P value of 2.0 to 8.2.

A C log P value is as described below.

A log P value is a common logarithm of a partition coefficient P. It is a physical property value showing how a certain compound is partitioned in equilibrium of two phase system consisting of oil (herein, n-octanol) and water by using a quantitative numerical value. The greater the log P value, the more the compound is hydrophobic, and the smaller the log P value, the more the compound is hydrophilic. Therefore, the log P value can be used as a parameter showing hydrophilicity and hydrophobicity of a compound.

$$\log P = \log(C_{oil}/C_{water})$$

$C_{oil}$ = molar concentration in oil phase
$C_{water}$ = molar concentration in water phase Although the log P value can be generally experimentally determined using n-octanol and water, in the present invention, a partition coefficient (C log P value) (calculated value) determined using a log P value estimation program is used. Specifically, in the present specification, a C log P value determined using "ChemBioDraw ultra ver. 12" is used.

The C log P value of the specific amine compound is preferably 3.5 to 6.5, more preferably 4.0 to 6.0, and even more preferably 4.5 to 5.5.

The method for causing the specific amine compound to have a C log P value of 2.0 to 8.2 is not particularly limited. Examples thereof include a method of adjusting the chain length of "linear or branched unsubstituted alkyl group" represented by X, a method of adjusting the chain length of "alkyl group which may have a substituent" represented by R, a method of introducing a hydrophilic group as the substituent of "alkyl group which may have a substituent" represented by R, and the like.

More specifically, a method of making the number of carbon atoms in X in General Formulae (1) and (2) less than 18, a method of introducing a hydrophilic group as a substituent of R in a case where the number of carbon atoms in X in General Formulae (1) and (2) is equal to or greater than 18, and the like can be exemplified.

Boiling Point

The boiling point of the specific amine compound is not particularly limited, but is preferably equal to or higher than 100° C. and more preferably equal to or higher than 200° C., because then the effects of the present invention are further improved. The boiling point refers to a value at 1 atm.

Molecular Weight

The molecular weight of the specific amine compound is not particularly limited, but is preferably 100 to 1,000 and more preferably 150 to 300, because then the effects of the present invention are further improved.

In the n-type thermoelectric conversion layer of the present invention, the content of the specific amine compound is not particularly limited. However, the content of the specific amine compound in the n-type thermoelectric conversion layer is preferably 5% to 95% by mass, more preferably 10% to 70% by mass, and even more preferably 20% to 50% by mass.

In the n-type thermoelectric conversion layer of the present invention, the content of the specific amine compound with respect to the content of the carbon nanotubes is not particularly limited. However, in the n-type thermoelectric conversion layer, the content of the specific amine compound with respect to the content of the carbon nanotubes is preferably 7.5% to 200% by mass, more preferably 12.5% to 150% by mass, and even more preferably 25% to 100% by mass.

Optional Components

The n-type thermoelectric conversion layer of the present invention may contain other components (a dispersion medium, an amine compound other than the specific amine compound, a polymer compound, a surfactant, an antioxidant, a lightfast stabilizer, a heat-resistant stabilizer, a plasticizer, and the like) in addition to CNT and the specific amine compound described above. The definitions, the specific examples, and the suitable aspects of the components are the same as those of the components contained in the composition for forming an n-type thermoelectric conversion layer that will be described later.

Substituent W

The substituent W in the present specification will be described.

The substituent W in the present specification is not particularly limited, and examples thereof include a halogen atom, an alkyl group (an alkyl group having 1 to 11 carbon atoms such as a methyl group, an ethyl group, a propyl group, a butyl group, a pentyl group, a hexyl group, a heptyl group, an octyl group, a nonyl group, a decyl group, or an undecyl group, a 2-ethyhexyl group, or the like), a cycloalkyl group (including a bicycloalkyl group, a tricycloalkyl group, or the like), an alkenyl group, a cycloalkenyl group, a 1-pentenyl group, a bicycloalkenyl group, an alkynyl group (including a 1-pentynyl group, a trimethylsilylethynyl group, a triethylsilylethynyl group, a tri-i-propylsilylethynyl group, a 2-p-propylphenylethynyl group, or the like), a cycloalkynyl group, an aryl group (including an aryl group having 6 to 20 carbon atoms such as a phenyl group, a naphthyl group, a p-pentylphenyl group, a 3,4-dipentylphenyl group, a p-heptoxyphenyl group, or a 3,4-diheptoxyphenyl group), a heterocyclic group (which may be referred to as a hetero ring group, including a 2-hexylfuranyl group or the like), a cyano group, a hydroxy group, a nitro group, an acyl group (including a hexanoyl group, a benzoyl group, or the like), an alkoxy group (including a butoxy group or the like), an aryloxy group, a silyloxy group, a heterocyclic oxy group, an acyloxy group, a carbamoyloxy group, an amino group (including an anilino group), an acylamino group, an aminocarbonylamino group (including a ureide group), alkoxy- and aryloxycarbonylamino groups, alkyl- or cycloalkyl- and arylsulfonylamino groups, a mercapto group, alkyl- or cycloalkyl- and arylthio groups (including a methylthio group, an octylthio group, or the like), a heterocyclic thio group, a sulfamoyl group, a sulfo group, alkyl- or cycloalkyl- and arylsulfinyl groups, alkyl- or cycloalkyl- and arylsulfonyl groups, alkyl- or cycloalkyl- and aryloxycarbonyl groups, a carbamoyl group, aryl- and heterocyclic azo groups, an imide group, a phosphino group, a phosphinyl group, a phosphinyloxy group, a phosphinylamino group, a phosphono group, a silyl group, a hydrazino group, and other known substituents. These substituents may further have the substituents described above.

Method for Manufacturing n-Type Thermoelectric Conversion Layer

The method for manufacturing the n-type thermoelectric conversion layer is not particularly limited, and examples thereof include a first suitable aspect, a second suitable aspect, and the like described below.

First Suitable Aspect

The first suitable aspect of the method for manufacturing the n-type thermoelectric conversion layer is a method of using a composition for forming an n-type thermoelectric conversion layer containing carbon nanotubes and the specific amine compound.

First, the composition will be described, and then the manufacturing method will be described.

Composition for Forming n-Type Thermoelectric Conversion Layer

As described above, the composition for forming an n-type thermoelectric conversion layer contains carbon nanotubes and the specific amine compound.

First, each of the components contained in the composition will be described, and then the method for preparing the composition will be described.

(1) Carbon Nanotubes

The definition, the specific examples, and the suitable aspect of the carbon nanotubes are as described above. The content of the carbon nanotubes in the composition for forming an n-type thermoelectric conversion layer is not particularly limited, but is preferably 0.1% to 20% by mass and more preferably 1% to 10% by mass with respect to the total amount of the composition. The content of the carbon nanotubes in the solid content is preferably 5% to 95% by mass, more preferably 30% to 90% by mass, and even more preferably 40% to 80% by mass. The aforementioned solid content means the components forming the thermoelectric conversion layer and does not include a solvent and a dispersant.

(2) Specific Amine Compound

The definition, the specific examples, and the suitable aspect of the specific amine compound are as described above. The content of the specific amine compound in the composition for forming an n-type thermoelectric conversion layer is not particularly limited, but is preferably 0.05% to 20% by mass and more preferably 0.1% to 10% by mass with respect to the total amount of the composition. The content of the specific amine compound in the solid content is preferably 5% to 95% by mass, more preferably 10% to 70% by mass, and even more preferably 20% to 50% by mass. The aforementioned solid content means the components forming the thermoelectric conversion layer and does not include a solvent and a dispersant.

(3) Dispersion Medium

It is preferable that the composition for forming an n-type thermoelectric conversion layer contains a dispersion medium in addition to the carbon nanotubes and the specific amine compound.

The dispersion medium (solvent) is not limited as long as it can disperse CNT, and water, an organic solvent, and a mixed solvent of these can be used. Examples of the organic solvent include an alcohol-based solvent, an aliphatic halogen-based solvent such as chloroform, an aprotic polar solvent such as dimethylformamide (DMF), N-methylpyrrolidone (NMP), or dimethylsulfoxide (DMSO), an aromatic solvent such as chlorobenzene, dichlorobenzene, benzene, toluene, xylene, mesitylene, tetralin, tetramethylbenzene, or pyridine, a ketone-based solvent such as cyclohexanone, acetone, or methyl ethyl ketone, an ether-based solvent such as diethylether, tetrahydrofuran (THF), t-butylmethylether, dimethoxyethane, or diglyme, and the like.

One kind of dispersion medium can be used singly, or two or more kinds thereof can be used in combination.

It is preferable that the dispersion medium has undergone deaeration. A dissolved oxygen concentration in the dispersion medium is preferably equal to or lower than 10 ppm. Examples of the deaeration method include a method of irradiating the dispersion medium with ultrasonic waves under reduced pressure, a method of performing bubbling using an inert gas such as argon, and the like.

In a case where a solvent other than water is used as the dispersion medium, it is preferable to perform deaeration in advance. A moisture amount in the dispersion medium is preferably equal to or less than 1,000 ppm, and more preferably equal to or less than 100 ppm. As the deaeration method for the dispersion medium, it is possible to use known methods such as a method using a molecular sieve and distillation.

The content of the dispersion medium in the composition for forming an n-type thermoelectric conversion layer with respect to the total amount of the composition is preferably 25% to 99.99% by mass, more preferably 30% to 99.95% by mass, and even more preferably 30% to 99.9% by mass.

As the dispersion medium, water or an alcohol-based solvent which has a C log P value equal to or smaller than 3.0 is suitably exemplified, because these excellently disperse the carbon nanotubes and further improve the characteristics (electric conductivity and thermoelectromotive force) of the n-type thermoelectric conversion layer. The C log P value is as described above.

The alcohol-based solvent means a solvent containing a —OH group (hydroxy group).

The C log P value of the alcohol-based solvent is equal to or smaller than 3.0. The C log P value is preferably equal to or smaller than 1.0, because then the CNT dispersibility is further improved, and the characteristics of the n-type thermoelectric conversion element are further improved. The lower limit of the C log P value is not particularly limited. In view of the aforementioned effects, the lower limit is preferably equal to or greater than −3.0, more preferably equal to or greater than −2.0, and even more preferably equal to or greater than −1.0.

(4) Other Components

The composition for forming an n-type thermoelectric conversion layer may contain an amine compound other than the specific amine compound, a polymer compound, a surfactant, an antioxidant, a lightfast stabilizer, a heat-resistant stabilizer, a plasticizer, and the like in addition to the components described above.

Examples of the polymer compound include a conjugated polymer and a non-conjugated polymer.

Examples of the surfactant include known surfactants (a cationic surfactant, an anionic surfactant, and the like). Among these, an anionic surfactant is preferable, and sodium deoxycholate is more preferable.

Examples of the antioxidant include IRGANOX 1010 (manufactured by Ciba-Geigy Japan Limited), SUMILIZER GA-80 (manufactured by Sumitomo Chemical Co., Ltd.), SUMILIZER GS (manufactured by Sumitomo Chemical Co., Ltd), SUMILIZER GM (manufactured by Sumitomo Chemical Co., Ltd.), and the like.

Examples of the lightfast stabilizer include TINUVIN 234 (manufactured by BASF SE), CHIMASS ORB 81 (manufactured by BASF SE), CYASORB UV-3853 (manufactured by SUN CHEMICAL COMPANY LTD.), and the like.

Examples of the heat-resistant stabilizer include IRGANOX 1726 (manufactured by BASF SE).

Examples of the plasticizer include ADEKASIZER RS (manufactured by ADEKA Corporation) and the like.

The content rate of the components other than the aforementioned dispersion medium with respect to the total amount of the composition is preferably 0.1% to 20% by mass, and more preferably 1% to 10% by mass.

Method for Preparing Composition for Forming n-Type Thermoelectric Conversion Layer The composition for forming an n-type thermoelectric conversion layer can be prepared by mixing the aforementioned components together. It is preferable that the composition is prepared by mixing together a dispersion medium, CNT, the specific amine compound, and other components which are used if necessary, and dispersing CNT.

The method for preparing the composition is not particularly limited and can be performed using a general mixing device or the like at room temperature and normal pressure. For example, the composition may be prepared by dissolving or dispersing the respective components in a solvent by stirring, shaking, or kneading. In order to accelerate the dissolution or dispersion, an ultrasonic treatment may be performed.

Furthermore, it is possible to improve the dispersibility of carbon nanotubes by means of heating the solvent to a temperature that is equal to or higher than room temperature and equal to or lower than a boiling point in the aforementioned dispersion step, extending the dispersion time, increasing the strength applied at the time of stirring, shaking, or kneading and the intensity of ultrasonic waves, and the like.

Manufacturing Method

The method for manufacturing the n-type thermoelectric conversion layer by using the composition for forming an n-type thermoelectric conversion layer is not particularly limited, and examples thereof include a method of coating a substrate with the aforementioned composition and forming a film, and the like.

The film forming method is not particularly limited, and it is possible to use known coating methods such as a spin coating method, an extrusion die coating method, a blade coating method, a bar coating method, a screen printing method, a stencil printing method, roll coating method, a curtain coating method, a spray coating method, a dip coating method, and an ink jet method.

If necessary, a drying step is performed after coating. For example, by exposing the film to the hot air, a solvent can be volatilized and dried.

Second Suitable Aspect

The second suitable aspect of the method for manufacturing the n-type thermoelectric conversion layer is a method in which an n-type thermoelectric conversion layer precursor is prepared using a composition for forming an n-type thermoelectric conversion layer precursor containing carbon nanotubes, and then the precursor is changed to an n-type through doping by using the aforementioned specific amine compound.

First, the composition will be described, and then the manufacturing method will be described.

Composition for Forming n-Type Thermoelectric Conversion Layer Precursor

As described above, the composition for forming an n-type thermoelectric conversion layer precursor contains carbon nanotubes. The definition, the specific examples, and the suitable aspect of the carbon nanotubes are as described above. The suitable aspect of the content of the carbon nanotubes in the composition is the same as that in the first suitable aspect described above.

It is preferable that the composition for forming an n-type thermoelectric conversion layer precursor contains a dispersion medium in addition to the carbon nanotubes. The specific examples and the suitable aspect of the dispersion medium are the same as those in the first suitable aspect described above.

The composition for forming an n-type thermoelectric conversion layer precursor may further contain other components. The specific examples and the suitable aspect of the aforementioned other components are the same as those in the first suitable aspect described above.

Manufacturing Method

The method for manufacturing the n-type thermoelectric conversion layer precursor by using the composition for forming an n-type thermoelectric conversion layer precursor is not particularly limited, and the specific examples and the suitable aspect of the method are the same as those of the method for manufacturing the n-type thermoelectric conversion layer in the first suitable aspect described above.

In the second suitable aspect, the n-type thermoelectric conversion layer precursor is prepared and then changed to an n-type through doping by using the specific amine compound described above. In this way, an n-type thermoelectric conversion layer is obtained.

The change to an n-type through doping is not particularly limited as long as it is a method of using the specific amine compound. Examples thereof include a method of immersing the n-type thermoelectric conversion layer precursor in a solution obtained by dissolving the aforementioned specific amine compound in a solvent, and the like. Specific examples of the solvent are the same as those of the dispersion medium described above.

The amount of the specific amine compound used is not particularly limited. However, the ratio of the specific amine compound, which is used for the change to an n-type through doping, with respect to the carbon nanotubes in the n-type thermoelectric conversion layer precursor is preferably 5% to 500% by mass, more preferably 10% to 200% by mass, and even more preferably 25% to 100% by mass.

If necessary, a drying step may be performed after the change to an n-type through doping. For example, by exposing the thermoelectric conversion layer to the hot air, the solvent can be volatilized and dried.

Thickness

From the viewpoint of causing a temperature difference and the like, the average thickness of the thermoelectric conversion layer of the present invention is preferably 1 to 500 μm, more preferably 2 to 300 μm, even more preferably 3 to 200 μm, and particularly preferably 5 to 100 μm.

The average thickness of the thermoelectric conversion layer can be determined by measuring thicknesses of the thermoelectric conversion layer at 10 random points and calculating an arithmetic mean thereof.

Thermoelectric Conversion Element

The constitution of the thermoelectric conversion element of the present invention is not particularly limited as long as the thermoelectric conversion element includes the n-type thermoelectric conversion layer described above.

In the thermoelectric conversion element of the present invention, the thermoelectric conversion layer may include only the aforementioned n-type thermoelectric conversion layer of the present invention described above or include, in addition to the n-type thermoelectric conversion layer, a p-type thermoelectric conversion layer (preferably a carbon nanotube-containing p-type thermoelectric conversion layer) electrically connected to the n-type thermoelectric conversion layer. As long as both the n-type thermoelectric conversion layer and the p-type thermoelectric conversion layer are electrically connected to each other, the thermoelectric conversion layers may come into direct contact with each other, or a conductor (for example, an electrode) may be disposed between them.

One of the examples of the structure of the thermoelectric conversion element of the present invention is the structure of the element shown in FIGS. 1 to 5. In the drawings, the arrow shows a direction of a temperature difference caused at the time of using the thermoelectric conversion element.

First Embodiment

FIG. 1 is a cross-sectional view of a first embodiment of the thermoelectric conversion element of the present invention.

In a thermoelectric conversion element 110 shown in FIG. 1, a pair of electrodes which includes a first electrode 13 and a second electrode 15 is disposed on a first substrate 12, and between the first electrode 13 and the second electrode 15, there is an n-type thermoelectric conversion layer 14 which contains carbon nanotubes and the specific amine compound described above. On the other surface of the second electrode 15, a second substrate 16 is disposed. On the outside of the first substrate 12 and the second substrate 16, metal plates 11 and 17 facing each other are disposed.

Second Embodiment

Figure 2:
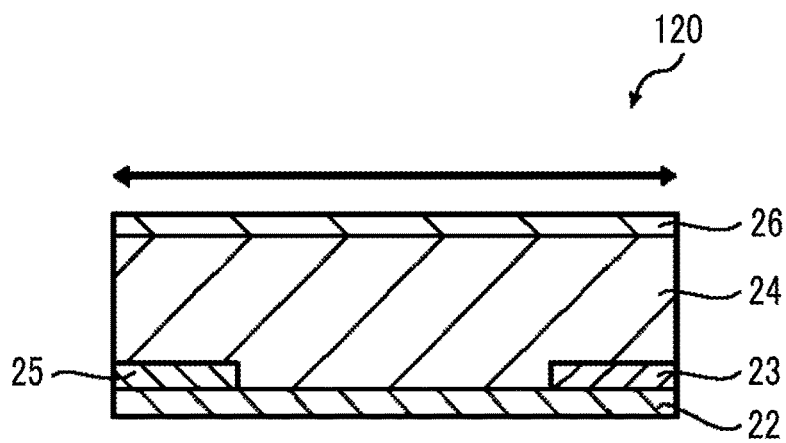
FIG. 2 is a cross-sectional view of a second embodiment of the thermoelectric conversion element of the present invention.

FIG. 2 is a cross-sectional view of a second embodiment of the thermoelectric conversion element of the present invention.

In a thermoelectric conversion element 120 shown in FIG. 2, a first electrode 23 and a second electrode 25 are disposed on a first substrate 22, and an n-type thermoelectric conversion layer 24, which contains carbon nanotubes and the aforementioned specific amine compound, is provided on the electrodes. The other surface of the n-type thermoelectric conversion layer 24 is provided with a second substrate 26.

Third Embodiment

Figure 3A:
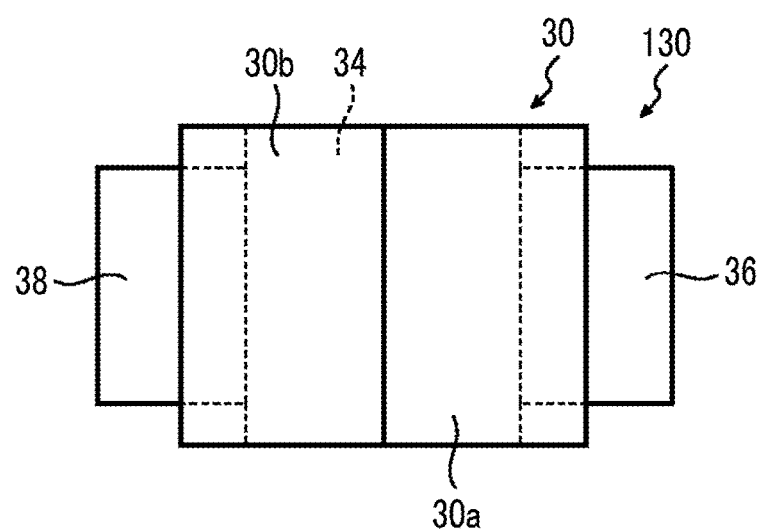
FIGS. 3A to 3C are conceptual views of a third embodiment of the thermoelectric conversion element of the present invention.
Figure 3B:
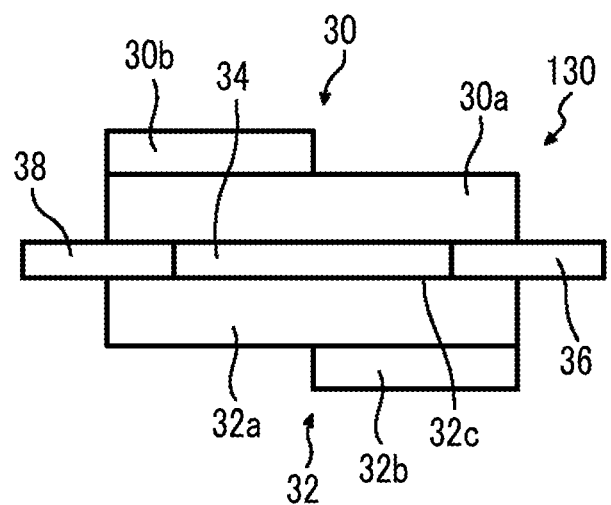
Figure 3C:
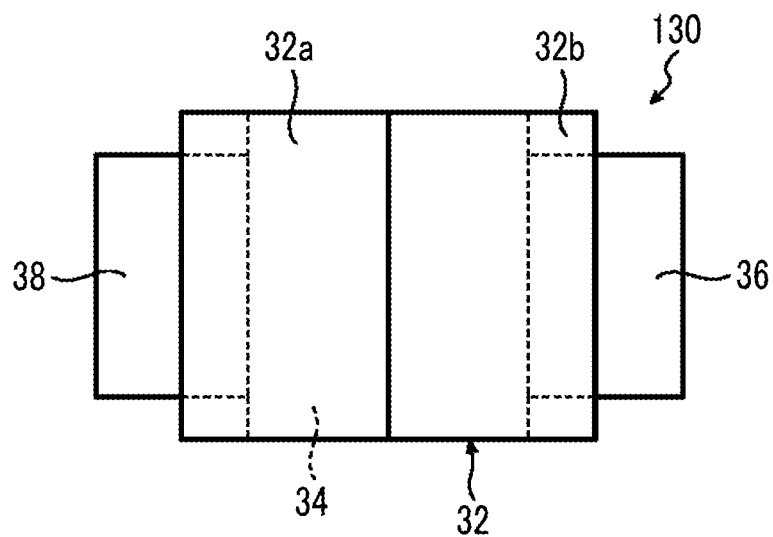

FIGS. 3A to 3C conceptually show a third embodiment of the thermoelectric conversion element of the present invention. FIG. 3A is a top view (a drawing obtained in a case where FIG. 3B is viewed from above the paper), FIG. 3B is a front view (a drawing obtained in a case where the thermoelectric conversion element is viewed from the plane direction of a substrate, which will be described later, and the like), and FIG. 3C is a bottom view (a drawing obtained in a case where FIG. 3B is viewed from the bottom of the paper).

As shown in FIGS. 3A to 3C, a thermoelectric conversion element 130 is basically constituted with a first substrate 32, an n-type thermoelectric conversion layer 34 containing carbon nanotubes and the aforementioned specific amine compound, a second substrate 30, a first electrode 36, and a second electrode 38.

Specifically, on a surface of the first substrate 32, the n-type thermoelectric conversion layer 34 is formed. Furthermore, on the surface of the first substrate 32, the first electrode 36 and the second electrode 38 (electrode pair) are formed which contact the n-type thermoelectric conversion layer 34 interposed between the electrodes in a substrate surface direction of the first substrate 32 (hereinafter, the substrate surface direction will be simply referred to as "plane direction" as well which is in other words a direction orthogonal to the direction along which the first substrate 32 and the second substrate 30 are laminated).

A pressure sensitive adhesive layer may be disposed between the first substrate 32 and the n-type thermoelectric conversion layer 34 or between the second substrate 30 and the n-type thermoelectric conversion layer 34, although the pressure sensitive adhesive layer is not shown in FIGS. 3A to 3C.

As shown in FIGS. 3A to 3C, the first substrate 32 includes a low thermal conduction portion 32a and a high thermal conduction portion 32b having a thermal conductivity higher than that of the low thermal conduction portion 32a. Likewise, the second substrate 30 includes a low thermal conduction portion 30a and a high thermal conduction portion 30b having a thermal conductivity higher than that of the low thermal conduction portion 30a.

In the thermoelectric conversion element 130, the two substrates are disposed such that the high thermal conduction portions thereof are in different positions in a direction along which the first electrode 36 and the second electrode 38 are separated from each other (that is, a direction along which electricity is conducted).

In a preferred aspect, the thermoelectric conversion element 130 has the second substrate 30 bonded through a pressure sensitive adhesive layer, and both the first substrate 32 and the second substrate 30 have a low thermal conduction portion and a high thermal conduction portion. The thermoelectric conversion element 130 has a constitution in which two sheets of substrates each having a high thermal conduction portion and a low thermal conduction portion are used such that the thermoelectric conversion layer is interposed between the two sheets of substrates in a state where the high thermal conduction portions of the two substrates are in different positions in the plane direction.

That is, the thermoelectric conversion element 130 is a thermoelectric conversion element which converts heat energy into electric energy by causing a temperature difference in the plane direction of the thermoelectric conversion layer (hereinafter, the thermoelectric conversion element will be referred to as an in plane-type thermoelectric conversion element as well). In the example illustrated in the drawing, by using a substrate including a low thermal conduction portion and a high thermal conduction portion having a thermal conductivity higher than that of the low thermal conduction portion, a temperature difference can be caused in the plane direction of the n-type thermoelectric conversion layer 34, and heat energy can be converted into electric energy.

Fourth Embodiment

Figure 4:
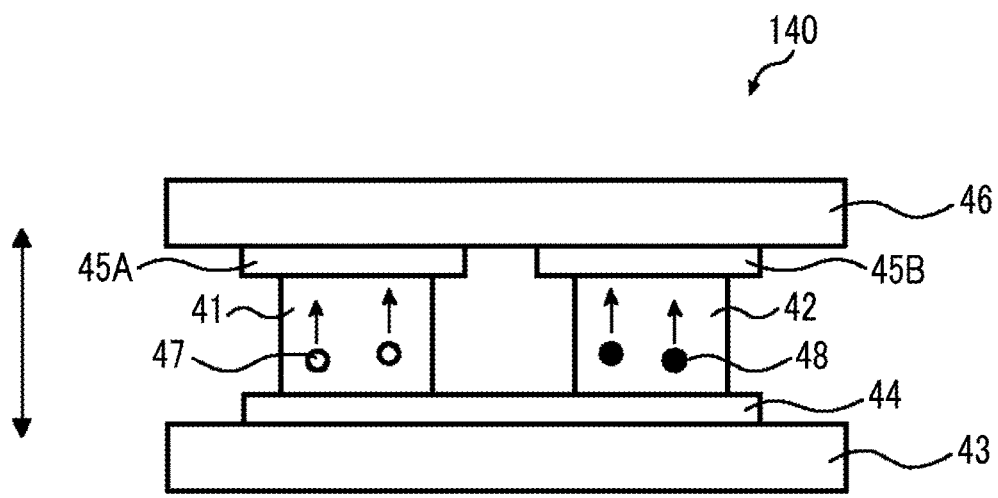
FIG. 4 is a conceptual view of a fourth embodiment of the thermoelectric conversion element of the present invention.

FIG. 4 conceptually shows a fourth embodiment of the thermoelectric conversion element.

A thermoelectric conversion element 140 shown in FIG. 4 has a p-type thermoelectric conversion layer (p-type thermoelectric conversion portion) 41 and an n-type thermoelectric conversion layer (n-type thermoelectric conversion portion) 42, and these layers are disposed in parallel to each other. The n-type thermoelectric conversion layer 42 is an n-type thermoelectric conversion layer containing carbon nanotubes and the aforementioned specific amine compound. The constitution of each of the p-type thermoelectric conversion layer 41 and the n-type thermoelectric conversion layer 42 will be specifically described later.

An upper end portion of the p-type thermoelectric conversion layer 41 is electrically and mechanically connected to a first electrode 45A, and an upper end portion of the n-type thermoelectric conversion layer 42 is electrically and mechanically connected to a third electrode 45B. On the outside of the first electrode 45A and the third electrode 45B, an upper substrate 46 is disposed. A lower end portion of each of the p-type thermoelectric conversion layer 41 and the n-type thermoelectric conversion layer 42 is electrically and mechanically connected to a second electrode 44 supported on a lower substrate 43. In this way, the p-type thermoelectric conversion layer 41 and the n-type thermoelectric conversion layer 42 are connected to each other in series through the first electrode 45A, the second electrode 44, and the third electrode 45B. That is, the p-type thermoelectric conversion layer 41 and the n-type thermoelectric conversion layer 42 are electrically connected to each other through the second electrode 44.

The thermoelectric conversion element 140 makes a temperature difference (in the direction of the arrow in FIG. 4) between the upper substrate 46 and the lower substrate 43, and as a result, for example, the upper substrate 46 side becomes a low-temperature portion, and the lower substrate 43 side becomes a high-temperature portion. In a case where such a temperature difference is made, in the p-type thermoelectric conversion layer 41, a hole 47 carrying a positive charge moves to the low-temperature portion side (upper substrate 46 side), and the potential of the first electrode 45A becomes higher than that of the second electrode 44. In contrast, in the n-type thermoelectric conversion layer 42, an electrode 48 carrying a negative charge moves to the low-temperature portion side (upper substrate 46 side), and the potential of the second electrode 44 becomes higher than that of the third electrode 45B. Consequently, a potential difference occurs between the first electrode 45A and the third electrode 45B, and for example, in a case where a load is connected to the end of the electrode, electric power can be extracted. At this time, the first electrode 45A becomes a positive electrode, and the third electrode 45B becomes a negative electrode.

Fifth Embodiment

Figure 5:
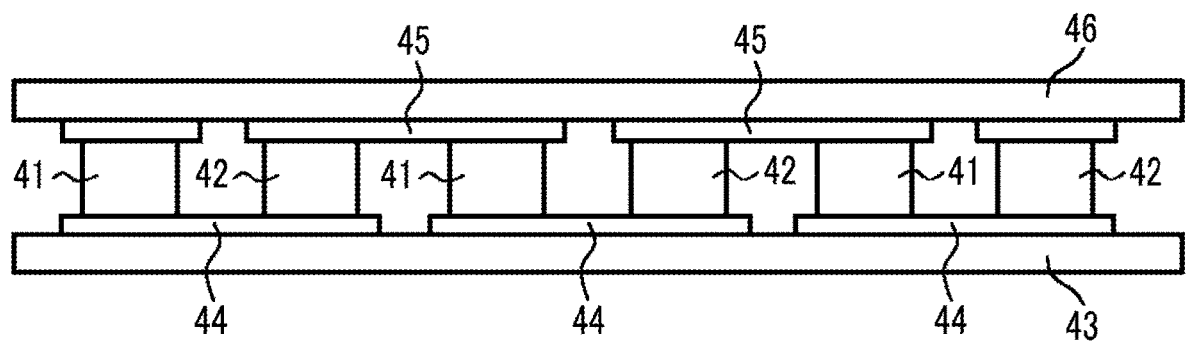
FIG. 5 is a conceptual view of a fifth embodiment of the thermoelectric conversion element of the present invention.

The thermoelectric conversion element 140 can obtain a higher voltage by, for example, alternately disposing a plurality of p-type thermoelectric conversion layers 41, 41 . . . and a plurality of n-type thermoelectric conversion layers 42, 42, . . . and connecting them to each other in series through the first and third electrodes 45 and the second electrode 44, as shown in FIG. 5.

As shown in FIG. 5, in the present invention, a plurality of thermoelectric conversion elements may be electrically connected to each other so as to constitute a so-called module (thermoelectric conversion module).

Hereinafter, each of the members constituting the thermoelectric conversion element will be specifically described.

Substrate

As the substrates in the thermoelectric conversion element (the first substrate 12 and the second substrate 16 in the first embodiment, the first substrate 22 and the second substrate 26 in the second embodiment, the low thermal conduction portions 32a and 30a in the third embodiment, and the upper substrate 46 and the lower substrate 43 in the fourth embodiment), substrates such as glass, transparent ceramics, and a plastic film, and the like can be used. In the thermoelectric conversion element of the present invention, it is preferable that the substrate has flexibility. Specifically, the substrate preferably has such flexibility that the substrate is found to have an MIT folding endurance of equal to or greater than 10,000 cycles by a measurement method specified by ASTM D2176. As the substrate has such flexibility, a plastic film is preferable, and specific examples thereof include a polyester film such as polyethylene terephthalate, polyethylene isophthalate, polyethylene naphthalate, polybutylene terephthalate, poly(1,4-cyclohexylenedimethylene-terephthalate), polyethylene-2,6-naphthalenedicarboxylate, or a polyester film of bisphenol A and isophthalic and terephthalic acids, a polycycloolefin film such as a ZEONOR film (trade name, manufactured by ZEON CORPORATION), an ARTON film (trade name, manufactured by JSR Corporation), or SUMILITE FS1700 (trade name, manufactured by Sumitomo Bakelite Co. Ltd.), a polyimide film such as KAPTON (trade name, manufactured by DU PONT-TORAY CO., LTD.), APICAL (trade name, manufactured by Kaneka Corporation), UPILEX (trade name, manufactured by UBE INDUSTRIES, LTD.), or POMIRAN (trade name, manufactured by Arakawa Chemical Industries, Ltd.), a polycarbonate film such as PUREACE (trade name, manufactured by TEIJIN LIMITED) or ELMEC (trade name, manufactured by Kaneka Corporation), a polyether ether ketone film such as SUMILITE FS1100 (trade name, manufactured by Sumitomo Bakelite Co. Ltd.), a polyphenyl sulfide film such as TORELINA (trade name, manufactured by TORAY INDUSTRIES, INC.), and the like. From the viewpoint of ease of availability, heat resistance (preferably equal to or higher than 100° C.), economic feasibility, and effects, commercially available polyethylene terephthalate, polyethylene naphthalate, various polyimide or polycarbonate films, and the like are preferable.

In view of handleability, durability, and the like, the thickness of the substrate is preferably 5 to 3,000 µm, more preferably 10 to 1,000 µm, even more preferably 12.5 to 500 µm, and particularly preferably 12.5 to 100 µm. In a case where the thickness of the substrate is within the above range, the thermal conductivity is not reduced, and the thermoelectric conversion layer is not easily damaged due to an external shock.

Electrode

As electrode materials forming the electrodes in the thermoelectric conversion element, it is possible to use a transparent electrode material such as Indium-Tin-Oxide (ITO) or ZnO, a metal electrode material such as silver, copper, gold, or aluminum, a carbon material such as CNT or graphene, an organic material such as poly(3,4-ethylene-dioxythiophene) (PEDOT)/polystyrene sulfonate (PSS), a conductive paste in which conductive fine particles of silver, carbon, and the like are dispersed, a conductive paste containing metal nanowires of silver, copper, or aluminum, and the like. Among these, a metal electrode material such as aluminum, gold, silver, or copper or a conductive paste containing these metals is preferable.

p-Type Thermoelectric Conversion Layer

As the p-type thermoelectric conversion layer included in the thermoelectric conversion element of the fourth embodiment, a known p-type thermoelectric conversion layer can be used. As materials contained in the p-type thermoelectric conversion layer, it is possible to appropriately use known materials (for example, a composite oxide such as $NaCo_2O_4$ or $Ca_3Co_4O_9$, a silicide such as $MnSi_{1.73}$, $Fe_{1-x}Mn_xSi_2$, $Si_{0.8}Ge_{0.2}$, or $\beta$-$FeSi_2$, skutterudite such as $CoSb_3$, $FeSb_3$, or $RFe_3CoSb_{12}$ (R represents La, Ce, or Yb), and a Te-containing alloy such as BiTeSb, PbTeSb, $Bi_2Te_3$, or PbTe) and CNT.

Specific examples of the method for forming (manufacturing) the n-type thermoelectric conversion layer are as described above.

Article for Thermoelectric Power Generation

The article for thermoelectric power generation of the present invention is an article for thermoelectric power generation using the thermoelectric conversion element of the present invention.

Specific examples of the article for thermoelectric power generation include a generator such as a hot spring heat power generator, a solar power generator, or a waste heat power generator, a power supply for a wrist watch, a power supply for driving a semiconductor, a power supply for a small sensor, and the like.

That is, the aforementioned thermoelectric conversion element of the present invention can be suitably used for the above purposes.

Composition for Forming n-Type Thermoelectric Conversion Layer

The definition, the specific examples, and the suitable aspect of the composition for forming an n-type thermoelectric conversion layer of the present invention are the same as those of the composition for forming an n-type thermoelectric conversion layer described above.

EXAMPLES

Hereinafter, the present invention will be more specifically described based on examples, but the present invention is not limited thereto.

Examples 1 to 17, 19, and 20 and Comparative Examples 1 to 3 (Method a)

Preparation of Composition for Forming n-Type Thermoelectric Conversion Layer

First, single-layer CNT was pretreated. Specifically, by using a mechanical homogenizer (manufactured by SMT Corporation, HIGH-FLEX HOMOGENiZER HF93), 500 mg of single-layer CNT (CNT described in Table 1) and 250 mL of acetone were mixed together for 5 minutes at 18,000 rpm, thereby obtaining a dispersion liquid. The dispersion liquid was filtered under reduced pressure by using a Buchner funnel and a suction bottle, thereby obtaining a cloth-like CNT film (buckypaper). The cloth-like CNT was cut in a size equal to or smaller than 1 cm and used for the preparation of a CNT dispersion liquid (composition for forming an n-type thermoelectric conversion layer) as the next step.

Then, 1,200 mg of sodium deoxycholate (manufactured by TOKYO CHEMICAL INDUSTRY CO., LTD.) as a dispersant and a compound (added in the amount described in Table 1) described in Table 1 as an amine compound were dissolved in 16 mL of water as a solvent, and 400 mg of the single-layer CNT (CNT described in Table 1) pretreated as described above was added thereto. The composition was mixed for 7 minutes by using a mechanical homogenizer (manufactured by SMT Corporation, HIGH-FLEX HOMOGENiZER HF93), thereby obtaining a premix. By using a thin film revolution-type high-speed mixer "FILMIX 40-40 model" (manufactured by PRIMIX Corporation), a dispersion treatment was performed on the obtained premix in a constant-temperature tank with a temperature of 10° C. for 2 minutes at a circumferential speed of 10 m/sec (seconds) and then for 5 minutes at a circumferential speed of 40 m/sec by a high-speed revolution thin film dispersion method. By using a rotation·revolution mixer (manufactured by THINKY CORPORATION, AWATORI RENTARO), the obtained dispersion composition was mixed for 30 seconds at 2,000 rpm and defoamed for 30 seconds at 2,200 rpm, thereby preparing a CNT dispersion liquid (composition for forming an n-type thermoelectric conversion layer).

Manufacturing of n-Type Thermoelectric Conversion Layer

A frame made of TEFLON (registered trademark) was attached to a glass substrate having a thickness of 1.1 mm and a size of 40 mm×50 mm, and the area in the frame was coated with the obtained composition for forming an n-type thermoelectric conversion layer. The substrate was dried for 30 minutes at 50° C. and then for 30 minutes at 120° C., then immersed in ethanol for 1 hour so as to remove the dispersant, and dried for 30 minutes at 50° C. and then for 150 minutes at 120° C., thereby obtaining a film (n-type thermoelectric conversion layer). The thickness of the obtained thermoelectric conversion layer was about 7 μm.

Example 18 and Comparative Example 4 (Method b)

Preparation of CNT Dispersion Liquid 1,200 mg of sodium deoxycholate (manufactured by TOKYO CHEMICAL INDUSTRY CO., LTD.) as a dispersant was dissolved in 16 mL of water as a solvent, and 400 mg of the single-layer CNT (CNT described in Table 1) pretreated as described above was added thereto. The composition was mixed for 7 minutes by using a mechanical homogenizer (manufactured by SMT Corporation, HIGH-FLEX HOMOGENiZER HF93), thereby obtaining a premix. By using a thin film revolution-type high-speed mixer "FILMIX 40-40 model" (manufactured by PRIMIX Corporation), a dispersion treatment was performed on the obtained premix in a constant-temperature tank with a temperature of 10° C. for 2 minutes at a circumferential speed of 10 m/sec and then for 5 minutes at a circumferential speed of 40 m/sec by a high-speed revolution thin film dispersion method. By using a rotation·revolution mixer (manufactured by THINKY CORPORATION, AWATORI RENTARO), the obtained dispersion composition was mixed for 30 seconds at 2,000 rpm and defoamed for 30 seconds at 2,200 rpm, thereby preparing a CNT dispersion liquid.

Preparation of n-Type Thermoelectric Conversion Layer Precursor

Subsequently, a frame made of TEFLON (registered trademark) was attached to a glass substrate having a thickness of 1.1 mm and a size of 40 mm×50 mm, and the area in the frame was coated with the CNT dispersion liquid. The substrate was dried for 30 minutes at 50° C. and then for 30 minutes at 120° C., then immersed in ethanol for 1 hour so as to remove the dispersant, and dried for 30 minutes at 50° C. and then for 150 minutes at 120° C., thereby obtaining a film (n-type thermoelectric conversion layer precursor).

Change to n-Type Through Doping

Thereafter, the amine compound (dissolved in the amount described in Table 1) described in Table 1 was dissolved in 10 ml of methyl ethyl ketone (MEK). The obtained film (n-type thermoelectric conversion layer precursor) was cut in 1 cm×1 cm and immersed in the solution. After 3 hours, the film was taken out and dried for 30 minutes at 50° C. and then for 150 minutes at 120° C., thereby obtaining a film (n-type thermoelectric conversion layer). The thickness of the obtained thermoelectric conversion layer was about 7 μm.

Evaluation

The obtained n-type thermoelectric conversion layer was evaluated as below.

Seebeck Coefficient and Electric Conductivity

The obtained n-type thermoelectric conversion layer was cut in 1 cm, and by using a thermoelectric characteristic measuring device MODEL RZ2001i (manufactured by OZAWA SCIENCE CO., LTD.), a Seebeck coefficient (thermoelectromotive force per absolute temperature of 1 K) and an electric conductivity at 80° C. and 120° C. were measured. By interpolation, a Seebeck coefficient and an electric conductivity at 100° C. were calculated. The results are shown in Table 1. The evaluation standards are as below.

Seebeck Coefficient

AA: less than −40 uV/K
A: equal to or greater than −40 uV/K and less than −35 uV/K
B: equal to or greater than −35 uV/K and less than −30 uV/K
C: equal to or greater than −30 uV/K and less than −25 uV/K
D: equal to or greater than −25 uV/K and less than 0 uV/K
E: equal to or greater than 0 uV/K (changed into a p-type)

Electric Conductivity

AA: equal to or higher than 600 S/cm
A: equal to or higher than 500 S/cm and less than 600 S/cm
B: equal to or higher than 400 S/cm and less than 500 S/cm
C: equal to or higher than 200 S/cm and less than 400 S/cm
D: less than 200 S/cm Power Factor (PF)

The power factor was calculated from the following equation.

(Power factor)=(electric conductivity)×(Seebeck coefficient)$^2$

The results are shown in Table 1. The evaluation standards are as below. The higher the power factor, the more preferable. For practical use, the thermoelectric conversion layers graded AA to C according to the following evaluation standards are preferable.

AA: equal to or higher than 100 uW/mK$^2$
A: equal to or higher than 65 uW/mK$^2$ and less than 100 uW/mK$^2$
B: equal to or higher than 35 uW/mK$^2$ and less than 65 uW/mK$^2$
C: equal to or higher than 25 uW/mK$^2$ and less than 35 uW/mK$^2$
D: equal to or higher than 10 uW/mK$^2$ and less than 25 uW/mK$^2$
E: less than 10 uW/mK$^2$ Performance Stability of n-Type Thermoelectric Conversion Layer Exposed to Moisture-Heat Environment for Long Period of Time The obtained n-type thermoelectric conversion layer was stored for 10 days in an environment with a temperature of 50° C. and a humidity of 90% (moisture-heat environment test). Then, a Seebeck coefficient thereof was measured. The Seebeck coefficient was measured by the method described above. Thereafter, from the Seebeck coefficients measured before and after the moisture-heat environment test, a rate of change (shown below) of a Seebeck coefficient caused by the moisture-heat environment test was calculated, and the performance stability of the n-type thermoelectric conversion layer exposed to a moisture-heat environment for a long period of time was evaluated. The results are shown in Table 1. The evaluation standards are as below. The lower the rate of change, the more preferable. For practical use, the n-type thermoelectric conversion layers graded AA to D according to the following evaluation standards are preferable.

Rate of change of Seebeck coefficient caused by moisture-heat environment test/%=$(X-Y)/X \times 100$ X=Seebeck coefficient before moisture-heat environment test
Y=Seebeck coefficient after moisture-heat environment test AA: less than 3%
A: equal to or higher than 3% and less than 5%
B: equal to or higher than 5% and less than 10%
C: equal to or higher than 10% and less than 20%
D: equal to or higher than 20% and less than 30%
E: equal to or higher than 30% and less than 100%
F: equal to or higher than 100% (changed to a p-type after the moisture-heat test)

TABLE 1

| | | | | | Amine compound | | | |
| | Method | CNT | Dispersant | Solvent | Type | Molecular weight | ClogP | Boiling point |
| --- | --- | --- | --- | --- | --- | --- | --- | --- |
| Example 1 | a | C1 | Sodium deoxycholate | Water | $nC_{12}H_{25}-NH_2$ | 185.35 | 5.155 | 247° C. to 249° C. |
| Example 2 | a | C1 | Sodium deoxycholate | Water | $nC_{12}H_{25}-NH_2$ | 185.35 | 5.155 | 247° C. to 249° C. |
| Example 3 | a | C1 | Sodium deoxycholate | Water | $nC_{12}H_{25}-NH_2$ | 185.35 | 5.155 | 247° C. to 249° C. |
| Example 4 | a | C1 | Sodium deoxycholate | Water | $nC_{12}H_{25}-NH_2$ | 185.35 | 5.155 | 247° C. to 249° C. |
| Example 5 | a | C1 | Sodium deoxycholate | Water | $nC_{12}H_{25}-NH_2$ | 185.35 | 5.155 | 247° C. to 249° C. |
| Example 6 | a | C1 | Sodium deoxycholate | Water | $nC_{12}H_{25}-NH_2$ | 185.35 | 5.155 | 247° C. to 249° C. |
| Example 7 | a | C1 | Sodium deoxycholate | Water | $nC_{16}H_{33}-NH_2$ | 241.46 | 5.155 | 330° C. |
| Example 8 | a | C1 | Sodium deoxycholate | Water | (branched alkyl)-OH | 173.3 | 2.5824 | 119° C./8 torr |
| Example 9 | a | C1 | Sodium deoxycholate | Water | (branched alkyl)-NH$_2$ | 129.24 | 2.909 | 169° C. |
| Example 10 | a | C1 | Sodium deoxycholate | Water | $nC_{12}H_{25}-N^{+}(CH_3)_2-O^{-}$ | 229.4 | 5.998 | Equal to or higher than 200° C. |
| Example 11 | a | C1 | Sodium deoxycholate | Water | $nC_8H_{17}-NH_2$ | 129.24 | 3.039 | 175° C. to 177° C. |
| Example 12 | a | C1 | Sodium deoxycholate | Water | $(nC_8H_{17})_2NH$ | 241.46 | 6.888 | 297° C. to 298° C. |

TABLE 1-continued

| | | Amine compound | | Evaluation result | | | |
|---|---|---|---|---|---|---|---|
| | | Method a: added amount Method b: dissolved amount [g] | Immersion solvent | Seebeck coefficient | Electric conductivity | PF | Performance stability of thermoelectric conversion layer exposed to moisture-heat environment for long period of time |
| Example 1 | | 0.03 | | A | A | A | AA |
| Example 2 | | 0.05 | | A | AA | A | AA |
| Example 3 | | 0.4 | | AA | AA | AA | AA |
| Example 4 | | 0.1 | | AA | AA | AA | AA |
| Example 5 | | 0.6 | | A | AA | A | A |
| Example 6 | | 0.8 | | A | A | A | A |
| Example 7 | | 0.4 | | AA | AA | AA | A |
| Example 8 | | 0.4 | | AA | AA | AA | A |
| Example 9 | | 0.4 | | A | AA | A | C |
| Example 10 | | 0.4 | | A | A | A | A |
| Example 11 | | 0.4 | | A | A | A | C |
| Example 12 | | 0.4 | | B | A | B | B |

TABLE 2

| | Method | CNT | Dispersant | Solvent | Amine compound | | | |
|---|---|---|---|---|---|---|---|---|
| | | | | | Type | Molecular weight | ClogP | Boiling point |
| Example 13 | a | C1 | Sodium deoxycholate | Water | 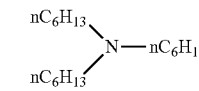 | 269.51 | 7.953 | 150° C./ 12 mmHg |
| Example 14 | a | C1 | Sodium deoxycholate | Water | 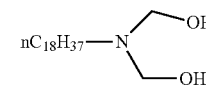 | 357.61 | 8.1802 | Equal to or higher than 200° C. |
| Example 15 | a | C1 | Sodium deoxycholate | Water | 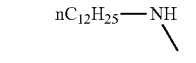 | 199.38 | 5.301 | 90° C./ 0.9 mmHg |
| Example 16 | a | C1 | Sodium deoxycholate | Water | | 185.35 | 4.779 | 234° C. |
| Example 17 | a | C1 | Sodium deoxycholate | Water | 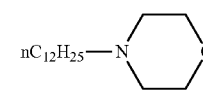 | 255.44 | 5.986 | 137° C./2 torr |
| Example 18 | b | C1 | Sodium deoxycholate | Water | $nC_{12}H_{25}$—$NH_2$ | 185.35 | 5.155 | 247° C. to 249° C. |
| Example 19 | a | C2 | Sodium deoxycholate | Water | $nC_{12}H_{25}$—$NH_2$ | 185.35 | 5.155 | 247° C. to 249° C. |
| Example 20 | a | C3 | Sodium deoxycholate | Water | $nC_{12}H_{25}$—$NH_2$ | 185.35 | 5.155 | 247° C. to 249° C. |
| Comparative Example 1 | a | C1 | Sodium deoxycholate | Water | $nC_{18}H_{37}$—$NH_2$ | 269.51 | 8.329 | 347° C. |
| Comparative Example 2 | a | C1 | Sodium deoxycholate | Water | Triethylamine | 101.19 | 1.605 | 90° C. |
| Comparative Example 3 | a | C1 | Sodium deoxycholate | Water | Tribenzylamine | 287.4 | 5.412 | 380° C. to 390° C. |
| Comparative Example 4 | b | C1 | Sodium deoxycholate | Water | Tribenzylamine | 287.4 | 5.412 | 380° C. to 390° C. |

TABLE 2-continued

|  | Amine compound | | Evaluation result | | | |
|---|---|---|---|---|---|---|
|  | Method a: added amount Method b: dissolved amount [g] | Immersion solvent | Seebeck coefficient | Electric conductivity | PF | Performance stability of thermoelectric conversion layer exposed to moisture-heat environment for long period of time |
| Example 13 | 0.4 |  | B | B | B | C |
| Example 14 | 0.4 |  | B | B | B | C |
| Example 15 | 0.4 |  | AA | AA | AA | AA |
| Example 16 | 0.4 |  | AA | A | AA | AA |
| Example 17 | 0.4 |  | AA | A | AA | AA |
| Example 18 | 0.05 | MEK | A | AA | A | AA |
| Example 19 | 0.4 |  | A | A | A | AA |
| Example 20 | 0.4 |  | AA | AA | AA | AA |
| Comparative Example 1 | 0.4 |  | B | C | C | F (separation of additive) |
| Comparative Example 2 | 0.4 |  | D | B | D | F |
| Comparative Example 3 | 0.4 |  | D | C | D | E |
| Comparative Example 4 | 0.05 | MEK | D | C | E | E |

Details of CNT in Table 1 are described in the following Table 2. The unit of the diameter distribution is nm. The GD ratio means the aforementioned G/D ratio. "e-Dips method" for C3 means "enhanced Direct Injection Pyrolytic Synthesis method".

TABLE 2

|  | C1 | C2 | C3 |
|---|---|---|---|
| Manufacturer | OCSiAl | OCSiAl | Meijo Nano Carbon Co., Ltd. |
| Manufacturing method | Arc method | Arc method | e-Dips method |
| Diameter | 1.34 nm | 1.85 nm | 1.43 nm |
| Diameter distribution | 1.10 to 1.68 nm | 1.30 to 4.01 nm | 1.18 to 2.51 nm |
| Diameter distribution width | 0.58 nm | 2.71 nm | 1.33 nm |
| GD ratio | 40.1 | 32.8 | 49.6 |

The descriptions regarding the amine compounds in Table 1 mean the following.

"n" described in "Type" means that the alkyl group is a linear (normal).

"C log P" means the C log P value of each of the amine compounds. The C log P value is as described above.

"Molecular weight" means the molecular weight of each of the amine compounds.

"Boiling point" means the boiling point of each of the amine compounds. Unless otherwise specified, the boiling point is a value at 1 atm.

All of the amine compounds used in the examples are represented by General Formula (1) or (2) described above and have a C log P value within a range of 2.0 to 8.2. Therefore, the compounds correspond to the specific amine compound described above. Although the amine compounds used in Comparative Examples 1 and 2 are represented by General Formula (1) described above, the C log P value thereof is outside the range of 2.0 to 8.2. Therefore, the compounds do not correspond to the specific amine compound described above. Furthermore, because the amine compounds used in Comparative Examples 3 and 4 are not represented by General Formula (1) or (2) described above, the amine compounds do not correspond to the specific amine compound described above.

In Table 1, "Immersion solvent" is a solvent used for the change to an n-type through doping in the method b.

As is evident from Table 1, Examples 1 to 18 containing the specific amine compound had a high power factor and exhibited excellent performance stability. Particularly, Examples 1 to 11 and 15 to 18, in which the specific amine compound had a C log P value of equal to or smaller than 6.5, exhibited a higher power factor. Among these, Examples 1 to 8, 10, and 15 to 18, in which the amine compound had a molecular weight of equal to or greater than 150, exhibited higher performance stability.

From the comparison between Examples 1 to 6, it was confirmed that Examples 3 and 4, in which the content of the amine compound was 25% to 100% by mass with respect to the content of the carbon nanotubes, exhibited a higher PF.

From the comparison between Examples 3 and 7, it was confirmed that Example 3, in which the amine compound had a molecular weight of equal to or smaller than 200, exhibited higher performance stability.

From the comparison between Examples 7 and 12, it was confirmed that Example 7, in which m in General Formula (1) was 1, exhibited higher performance stability and a higher PF.

From the comparison between Examples 3, 19, and 20, it was confirmed that Examples 3 and 20, in which the carbon nanotubes had a diameter of equal to or smaller than 1.5 nm and the width of the diameter distribution was equal to or smaller than 2.0 nm, exhibited a higher PF.

In contrast, although Comparative Example 1 containing an amine compound, which is represented by General Formula (1) described above and has a C log P value greater than 8.2, instead of the specific amine compound exhibited a sufficient power factor, a Seebeck coefficient thereof greatly changed due to the moisture-heat test, and the performance stability was insufficient. Presumably, this is because the amine compound eluted after the moisture-heat test, and the thermoelectric conversion layer was changed to a p-type.

Comparative Example 2 containing an amine compound, which is represented by General Formula (1) described above and has a C log P value of less than 2.0, instead of the specific amine compound exhibited a low power factor and insufficient performance stability.

Comparative Example 3 or 4 containing an amine compound other than the amine compound represented by General Formula (1) or (2) described above instead of the specific amine compound exhibited a low power factor and insufficient performance stability.

Thermoelectric Conversion Element

An n-type thermoelectric conversion element and a p-n junction thermoelectric conversion element were prepared as below. The n-type thermoelectric conversion layer was formed according to the same procedure as that in the examples and comparative examples described above. In this way, the n-type thermoelectric conversion element and the p-n junction thermoelectric conversion element corresponding to each of the examples and the comparative examples described above were prepared and evaluated in the same manner as that described above.

As a result, the same results as those shown in Table 1 were obtained, and it was confirmed that even in a case where the n-type thermoelectric conversion layer is used for preparing the n-type thermoelectric conversion element and the p-n junction thermoelectric conversion element, a high power factor and excellent performance stability are exhibited.

n-Type Thermoelectric Conversion Element

As a substrate, a glass substrate having a thickness of 1.1 mm and a size of 40 mm×50 mm was used. The substrate was subjected to ultrasonic cleaning in acetone and then subject to a UV-ozone treatment for 10 minutes. Thereafter, a first electrode and a second electrode made of gold having a size of 30 mm×5 mm and a thickness of 10 nm were formed on each of both end portion sides of the substrate.

A frame made of TEFLON (registered trademark) was attached onto a substrate on which the electrodes were formed, and the CNT dispersion liquid prepared as described above was poured into the area in the frame. The substrate was dried for 30 minutes at 50° C. and then for 30 minutes at 120° C., immersed in ethanol for 1 hour so as to remove the dispersant, and dried for 30 minutes at 50° C. and then for 150 minutes at 120° C. After drying, the frame was detached, an n-type thermoelectric conversion layer having a thickness of about 7 μm was formed (for the method b, the change to an n-type through doping was also performed to form the n-type thermoelectric conversion layer), thereby preparing a thermoelectric conversion element 120 (n-type thermoelectric conversion element) constituted as shown in FIG. 2.

p-n Junction Thermoelectric Conversion Element

Composition for Forming p-Type Thermoelectric Conversion Layer 1,200 mg of sodium deoxycholate (manufactured by TOKYO CHEMICAL INDUSTRY CO., LTD.) as a dispersant was dissolved in 16 mL of water as a solvent, and 400 mg of the single-layer CNT (Tuball manufactured by OCSiAl) pretreated as described above was added thereto. The composition was mixed for 7 minutes by using a mechanical homogenizer (manufactured by SMT Corporation, HIGH-FLEX HOMOGENiZER HF93), thereby obtaining a premix. By using a thin film revolution-type high-speed mixer "FILMIX 40-40 model" (manufactured by PRIMIX Corporation), a dispersion treatment was performed on the obtained premix in a constant-temperature tank with a temperature of 10° C. for 2 minutes at a circumferential speed of 10 m/sec and then for 5 minutes at a circumferential speed of 40 m/sec by a high-speed revolution thin film dispersion method. By using a rotation·revolution mixer (manufactured by THINKY CORPORATION, AWATORI RENTARO), the obtained dispersion composition was mixed for 30 seconds at 2,000 rpm and defoamed for 30 seconds at 2,200 rpm, thereby preparing a CNT dispersion liquid (composition for forming a p-type thermoelectric conversion layer).

Preparation of p-Type Thermoelectric Conversion Element

By using the composition for forming a p-type thermoelectric conversion layer as a dispersion liquid, a p-type thermoelectric conversion element was prepared through the same preparation step as that used for preparing the thermoelectric conversion element 120.

Preparation of p-n Junction Thermoelectric Conversion Element

The electrodes in the thermoelectric conversion element 120 were connected to the electrodes in the p-type thermoelectric conversion element through a conductive wire, thereby preparing a p-n junction thermoelectric conversion element (thermoelectric conversion element in which the p-type thermoelectric conversion layer and the n-type thermoelectric conversion layer are electrically connected to each other).

EXPLANATION OF REFERENCES 110, 120, 130, 140: thermoelectric conversion element
11, 17: metal plate
12, 22: first substrate
13, 23: first electrode
14, 24: n-type thermoelectric conversion layer
15, 25: second electrode
16, 26: second substrate
30: second substrate
32: first substrate
32a, 30a: low thermal conduction portion
32b, 30b: high thermal conduction portion
34: n-type thermoelectric conversion layer
36: first electrode
38: second electrode
41: p-type thermoelectric conversion layer
42: n-type thermoelectric conversion layer
43: lower substrate
44: second electrode
45: first and third electrodes
45A: first electrode
45B: third electrode
46: upper substrate
47: hole
48: electron

What is claimed is:

1. An n-type thermoelectric conversion layer comprising:
   carbon nanotubes; and
   an amine compound which is represented by General Formula (1) or (2) and has a C log P value of 2.0 to 8.2,

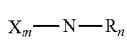  (1)

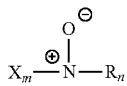  (2)

in General Formulae (1) and (2),

X represents a linear or branched unsubstituted alkyl group wherein the number of carbon atoms in the alkyl group is 1 to 30, R represents a hydrogen atom or an alkyl group which may have a substituent wherein the number of carbon atoms in the alkyl group is 1 to 10, m represents an integer of 1 to 3, in a case where m is an integer equal to or greater than 2, a plurality of X's may be the same as or different from each other, n represents an integer of 0 to 2, in a case where n is an integer equal to or greater than 2, a plurality of R's may be the same as or different from each other and may form a ring by being bonded to each other, and m and n satisfy a relation equation of m+n=3.

2. The n-type thermoelectric conversion layer according to claim 1,
   wherein the amine compound is represented by General Formula (1), and
   m in General Formula (1) is 1.

3. The n-type thermoelectric conversion layer according to claim 1,
   wherein a boiling point of the amine compound is equal to or higher than 200° C.

4. A thermoelectric conversion element comprising:
   the n-type thermoelectric conversion layer according to claim 1.

5. The thermoelectric conversion element according to claim 4, further comprising:
   a p-type thermoelectric conversion layer electrically connected to the n-type thermoelectric conversion layer, wherein the p-type thermoelectric conversion layer contains carbon nanotubes.

6. A composition for forming an n-type thermoelectric conversion layer, comprising:
   carbon nanotubes; and
   an amine compound which has a C log P value of 2.0 to 8.2 and is represented by General Formula (1) or (2),

  (1)

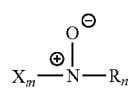  (2)

in General Formulae (1) and (2),

X represents a linear or branched unsubstituted alkyl group wherein the number of carbon atoms in the alkyl group is 1 to 30, R represents a hydrogen atom or an alkyl group which may have a substituent wherein the number of carbon atoms in the alkyl group is 1 to 10, m represents an integer of 1 to 3, in a case where m is an integer equal to or greater than 2, a plurality of X's may be the same as or different from each other, n represents an integer of 0 to 2, in a case where n is an integer equal to or greater than 2, a plurality of R's may be the same as or different from each other and may form a ring by being bonded to each other, and m and n satisfy a relation equation of m+n=3.

7. The n-type thermoelectric conversion layer according to claim 2,
   wherein a boiling point of the amine compound is equal to or higher than 200° C.

8. A thermoelectric conversion element comprising:
   the n-type thermoelectric conversion layer according to claim 2.

9. A thermoelectric conversion element comprising:
   the n-type thermoelectric conversion layer according to claim 3.

10. A thermoelectric conversion element comprising:
    the n-type thermoelectric conversion layer according to claim 7.

* * * * *